April 18, 1972 H. E. KENDALL Plant Pat. 3,116
AVOCADO TREE
Filed March 6, 1970
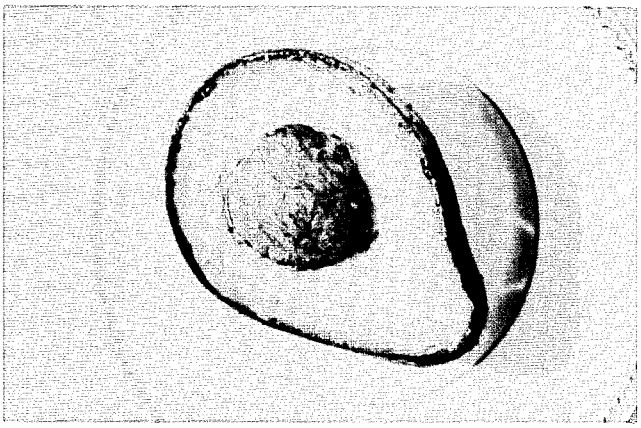
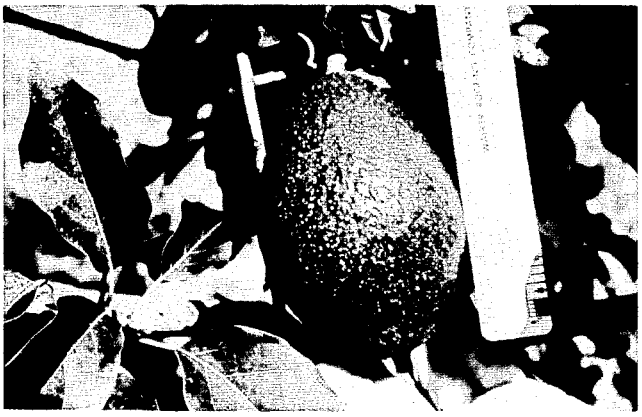
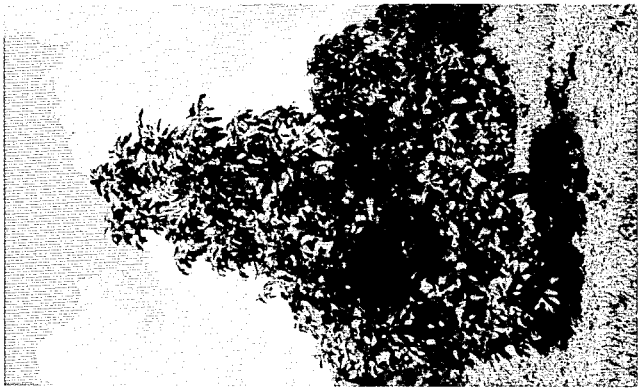
Harold E. Kendall
INVENTOR
BY Clarence A. O'Brien and Harvey B. Jacobson
Attorneys United States Patent Office Plant Pat. 3,116
Patented Apr. 18, 1972

3,116
AVOCADO TREE

Harold E. Kendall, P.O. Box 458,
Goulds, Fla. 33170

Filed Mar. 6, 1970, Ser. No. 17,350
Int. Cl. A01h 5/03
U.S. Cl. Plt.—44 1 Claim

This invention pertains to a new and distinct variety of avocado tree which has many highly desirable characteristics. This new variety originated in my groves in Dade County, Fla., from a seedling of Guatemalan-West Indian parentage. The new variety has been asexually reproduced in my groves in Dade County, Fla. by budding and grafting without apparent variation.

The accompanying identifications show a specimen of the fruit, a cross section thereof, and the mature tree.

This new avocado variety matures at a time when there are very few or no commercially grown avocados of similar size and eating quality available from the Florida production area. This makes it of great economic value to the industry by lengthening the marketing season and by giving the industry a fruit that is of competitive size and comparative quality with fruit grown in other areas at this time of year.

The tree is a vigorous growing tree with an upright habit, but branches freely and low to the ground. The fruit is borne on short stems (3") attached to the fruit at a slight angle. It is borne singly or in small clusters and tends to hang on the inside of the tree, well protected from the sun. It is small to medium size, 10 oz. and 4½" to 5" long. It is dark green in color, slightly pebbled and with prominent lenticels. The shape varies from oblong-ovate to slightly pyriform.

This new variety of avocado bears heavily and regularly each year, holding its crop until the end of March. Harvesting can commence in late December. The fruit appears to have a long softening period. It frequently takes 8 to 10 days for the fruit to soften after being severed from the tree. This will enable the fruit to be shipped satisfactorily to many markets which are a long distance from the producing area.

This new variety is quite free from avocado scab and other diseases. The seed is brown in color, medium size and tight in the cavity. The flesh is of excellent buttery taste and smooth texture, free of fibre. It ranges in color from deep yellow close to the seed to light green next to the skin. After softening, the flesh appears to keep firm and of good quality for several days.

The leaves are alternate and the nodes close together (¾" or less). They are lanceolate or ovate in shape becoming acuminate or acute at the apex. Margins are entire and silghtly undulate. It has perfect flowers and has been classified as a B variety. It flowers very early in the spring, usually beginning mid-February to early March. The fruit usually matures in January. It has been noted that frequently the trees are blooming and setting a new crop of small fruit while holding the previous crop on the tree. It is precocious in its bearing habits, frequently setting fruit in its second year of growth. The tree is propagated easily by either budding or grafting.

Having thus disclosed my invention, I claim:

1. The new and distinct variety of avocado tree, substantially as shown and described, characterized particularly by its vigorous, thrifty, upright but freely branching growth; the tendency of the fruit to grow on the inside of the tree; the early blooming and seeding of heavy crop of fruit early each year and carrying crop to maturity late in the season; the fruit being further characterized as from oblong-ovate to slightly pyriform with flesh of smooth texture, free of fibre and excellent buttery taste.

No references cited.

ROBERT E. BAGWILL, Primary Examiner